(12) United States Patent
Jenkins et al.

(10) Patent No.: US 9,232,973 B2
(45) Date of Patent: Jan. 12, 2016

(54) ELECTROSURGICAL INSTRUMENT

(75) Inventors: Andrew Edward Jenkins, Rhondda Cynon Tarff (GB); Kerry Simpson Briggs, Cardiff (GB); Philip John Warren, Rhondda Cyon Taff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 687 days.

(21) Appl. No.: 13/393,984

(22) PCT Filed: Nov. 10, 2011

(86) PCT No.: PCT/GB2011/001590
§ 371 (c)(1),
(2), (4) Date: Mar. 27, 2012

(87) PCT Pub. No.: WO2012/066276
PCT Pub. Date: May 24, 2012

(65) Prior Publication Data
US 2012/0283723 A1 Nov. 8, 2012

(30) Foreign Application Priority Data
Nov. 19, 2010 (GB) .................................. 1019554.3

(51) Int. Cl.
*A61B 18/14* (2006.01)
(52) U.S. Cl.
CPC ........... *A61B 18/14* (2013.01); *A61B 2018/141* (2013.01)
(58) Field of Classification Search
CPC ................................................ A61B 2018/141
See application file for complete search history.

(56) References Cited

U.S. PATENT DOCUMENTS

| 4,493,320 | A | 1/1985 | Treat |
| 4,905,691 | A | 3/1990 | Rydell |
| 5,078,716 | A | 1/1992 | Doll |
| 2007/0198011 | A1 | 8/2007 | Sugita |

(Continued)

FOREIGN PATENT DOCUMENTS

| CN | 1805716 A | 7/2006 |
| CN | 101061970 A | 10/2007 |

(Continued)

OTHER PUBLICATIONS

Search Report issued in British Patent Application No. 1019554.3 dated Feb. 17, 2011.

(Continued)

*Primary Examiner* — Michael Kahelin
(74) *Attorney, Agent, or Firm* — Oliff PLC

(57) ABSTRACT

A bipolar snare including an elongated tubular electrically insulating sheath, a pair of elongated flexible electrically conductive wires disposed within the sheath, and an electrically insulating connector disposed at the distal ends of the wires mechanically connecting the distal ends of the wires to form a loop projecting from the distal end of the sheath. The wires are provided with electrical insulation covering all but a selected portion of each of the wires. The device also includes a guide member located within the sheath and forming compartments for each of the electrically conductive wires, the guide member being rotatable within the sheath. The guide member is also set back from the distal end of the sheath to an extent such that the whole of the loop including at least part of the connector is capable of being received within the sheath.

9 Claims, 10 Drawing Sheets

(56) References Cited

U.S. PATENT DOCUMENTS

| | | |
|---|---|---|
| 2008/0234693 A1 | 9/2008 | Stefanchik |
| 2009/0036899 A1 | 2/2009 | Carlton et al. |
| 2010/0036375 A1* | 2/2010 | Regadas .......................... 606/39 |

FOREIGN PATENT DOCUMENTS

| | | |
|---|---|---|
| DE | 199 38 902 A1 | 4/2000 |
| EP | 0 467 501 A1 | 1/1992 |
| EP | 1 864 623 A1 | 12/2007 |
| JP | H02-291850 A | 12/1990 |
| JP | H04-241853 A | 8/1992 |
| JP | 2010-082298 A | 4/2010 |
| WO | WO 00/42926 A1 | 7/2000 |
| WO | 2009/099960 A1 | 8/2009 |

OTHER PUBLICATIONS

International Search Report issued in International Patent Application No. PCT/GB2011/001590 mailed Jul. 4, 2012.

Written Opinion of the International Searching Authority issued in International Patent Application No. PCT/GB2011/001590 date Jul. 4, 2012.

Jan. 22, 2015 Office Action issued in Chinese Patent Application No. 201180055284.9.

Aug. 4, 2015 Office Action issued in Japanese Patent Application No. 2013-539328.

May 26, 2015 Office Action issued in Australian Patent Application No. 2011330949.

\* cited by examiner

ELECTROSURGICAL INSTRUMENT

TECHNICAL FIELD

This invention relates to an electrosurgical instrument and in particular to a bipolar snare device.

BACKGROUND TO THE INVENTION

Bipolar snares are known, and examples are given in U.S. Pat. Nos. 4,493,320, 4,905,691 and 5,078,716. Each of these designs have a pair of wires extending from an elongate sheath, the wires being separated by an insulating divider to form first and second bipolar electrodes. An electrosurgical current flows between the wires, cutting the tissue as the wires are drawn into the sheath.

Each of the above designs, however, suffers from difficulties in completing the cutting of tissue as the wires are drawn against the end of the sheath.

U.S. Pat. No. 5,078,716 describes a bipolar snare in which the loop and connector are be received within the sheath. However, when the wires are withdrawn within the sheath there is a risk of the wires becoming twisted resulting in shorting between the wires. This is countered by an additional section of insulation adjacent the connector. This additional insulation prevents shorting between the wires, but results in the less efficient cutting of tissue, especially when the wires are very close to the sheath.

EP047501A illustrates a bipolar snare with a rotatable guide member, but in this device the guide member prevents the whole of the loop including the insulating connector from being withdrawn within the sheath. Thus the cutting effectiveness of the snare device, particularly when the wires are close to the end of the sheath, is reduced.

SUMMARY OF THE INVENTION

The present invention attempts to address the various shortcomings of the prior art.

Accordingly, a bipolar snare device is provided, the snare device comprising an elongated tubular electrically insulating sheath having a proximal and a distal end, a pair of elongated flexible electrically conductive wires with the wires disposed within the sheath and each having proximal and distal ends and having a length such that the wires can each extend from at least the distal end of the sheath, an electrically insulating connector disposed at the distal ends of the wires mechanically connecting the distal ends of the wires to form a loop projecting from the distal end of the sheath and with the wires electrically insulated from each other, the wires meeting the connector at first and second locations, electrical insulation disposed covering all but a selected portion of each of the elongated wires which form the loop, a handle for sliding the wires relative to the sheath to expand or contract the loop, and electrical connections for connecting the proximal ends of the wires to a bipolar electrosurgical generator, wherein the device also includes a guide member located within the sheath and forming compartments for each of the electrically conductive wires, the guide member being rotatable within the sheath to prevent the electrically conductive wires from becoming twisted one about the other, the guide member being arranged such that the whole of the loop including at least part of the electrically insulating connector is capable of being received within the sheath, such that the first and second locations where the wires meet the connector can be received within the sheath. The first and second locations where the wires meet the electrically insulating connector are preferably substantially at the same axial position with respect to one another.

One advantageous feature of embodiments of the present invention is that the guide member prevents the electrically conductive wires from becoming twisted, but still allows the loop including at least part of the insulating connector to be received within the sheath.

In addition, the guide member of embodiments of the present invention also prevents shorting between the wires, and yet still allows for efficient tissue cutting, even when the wires are very close to the end of the sheath.

In one embodiment the guide member is set back from the distal end of the sheath to an extent that the whole of the loop can be received within the sheath.

In some embodiments of the present invention, the guide member conveniently comprises a cylindrical member with an I-shaped cross section forming two compartments, one for each of the electrically conductive wires. In this way, the wires are each contained separately within their own compartment, preventing the two wires from coming into contact with each other. If the wires are rotated, the guide member rotates within the sheath to maintain the separation of the wires one from the other.

Alternatively, the guide member conceivably comprises a cylindrical member with two lumens therein, one for each of the electrically conducting wires. Whichever type of guide member is employed, it maintains separation of the wires while rotating within the sheath when required.

In a particularly advantageous construction, the guide member is provided with an extension at its distal end, the extension being capable of separating the electrically conductive wires as they exit the guide member. The extension is conveniently in the form of a planar partition, and is preferably movable between two positions, a first extended position, and a second retracted position to provide space for the electrically insulating connector to at least partly enter the sheath. The extension is conveniently formed of a flexible material, capable of collapsing into its second position. In this way, the extension separates the conductive wires, while collapsing to allow the whole of the loop, including some or all of the insulating connector, to enter the sheath. Whether in its first or second position, the extension separates the two wires, and yet is still rotatable within the sheath.

The extension need not necessarily be formed by a separate member, but may be integral with the remainder of the guide member. Conceivably, the extension can be the same cross-section as the remainder of the guide member, merely being made more flexible in some way, or otherwise movable with respect to the remainder of the guide member.

Embodiments of the invention further reside in a bipolar snare device comprising an elongated tubular electrically insulating sheath having a proximal and a distal end, a pair of elongated flexible electrically conductive wires with the wires disposed within the sheath and each having proximal and distal ends and having a length such that the wires can each extend from at least the distal end of the sheath, an electrically insulating connector disposed at the distal ends of the wires mechanically connecting the distal ends of the wires to form a loop projecting from the distal end of the sheath and with the wires electrically insulated from each other, electrical insulation disposed covering all but a selected portion of each of the elongated wires which form the loop, a handle for sliding the wires relative to the sheath to expand or contract the loop, and electrical connections for connecting the proximal ends of the wires to a bipolar electrosurgical generator, characterised in that the device also includes a guide member located within the sheath and forming compartments for each of the electrically conductive wires, the guide member being rotatable within the sheath to prevent the electrically conductive wires from becoming twisted one about the other, the guide member being provided with an extension at its distal end, the extension being capable of separating the electrically conductive wires as they exit the guide member.

As before, the guide member conveniently comprises a cylindrical member with an I-shaped cross section forming two compartments, one for each of the electrically conductive wires, or alternatively a cylindrical member with two lumens therein, one for each of the electrically conducting wires. Similarly, the extension is conveniently in the form of a planar partition, and movable between two positions, a first extended position in which it separates the electrically conductive wires, and a second retracted position to provide space for the electrically insulating connector to at least partly enter the sheath. As before, the extension is preferably formed of a flexible material, capable of collapsing into its second position. The extension on the guide member maintains the separation of the two wires, while the ability to move between two positions allows for the whole of the loop, including some or all of the insulating connector, to be withdrawn into the sheath, maintaining the cutting efficiency of the device throughout the whole of the cutting process.

DESCRIPTION OF THE DRAWINGS

Embodiments of the invention will now be further described, by way of example only, with reference to the accompanying drawings, in which.

EMBODIMENTS OF THE INVENTION

Figure 1:
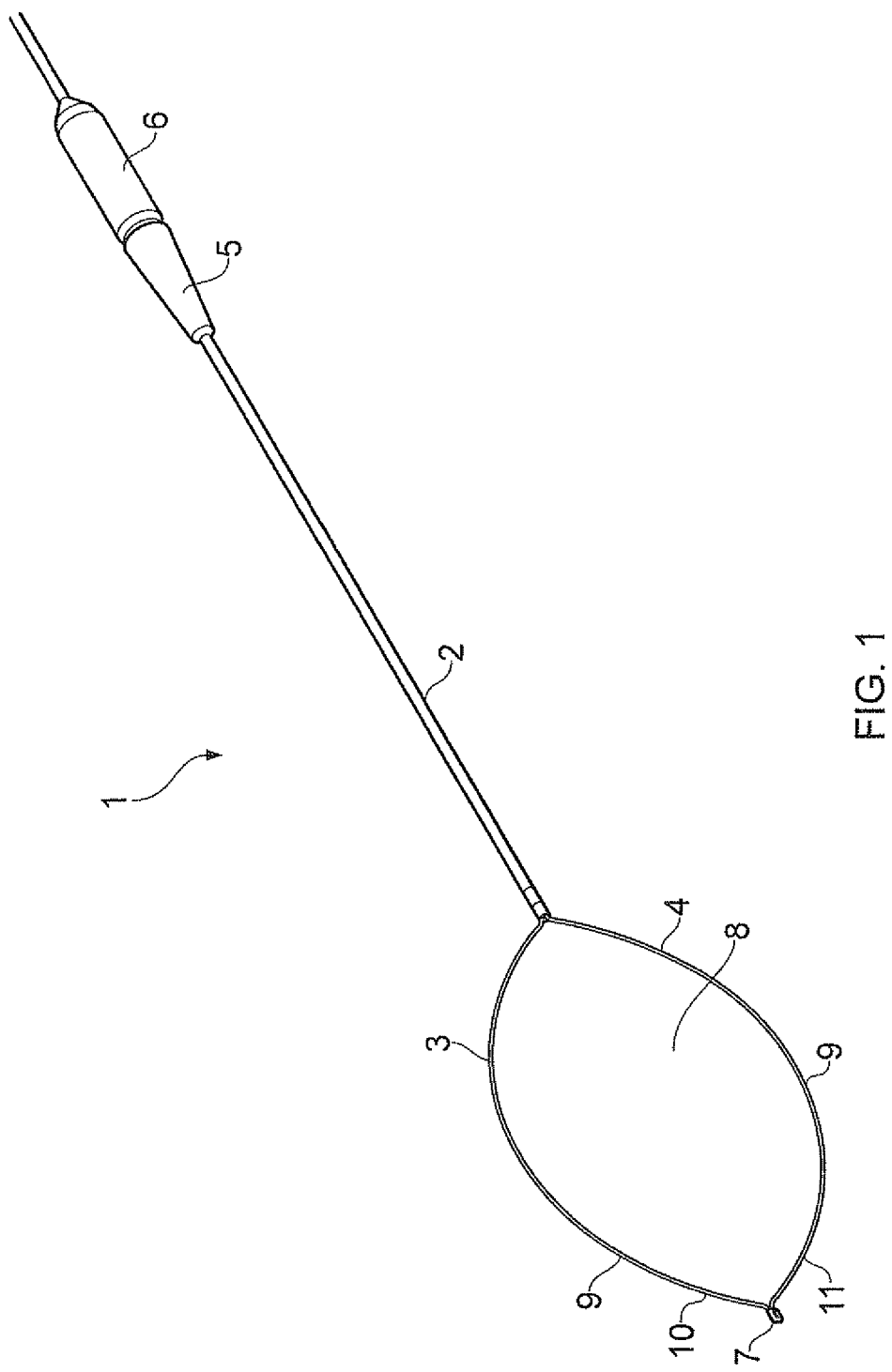
FIG. 1 is a perspective view of a bipolar snare in accordance with the present invention.
Figure 2:
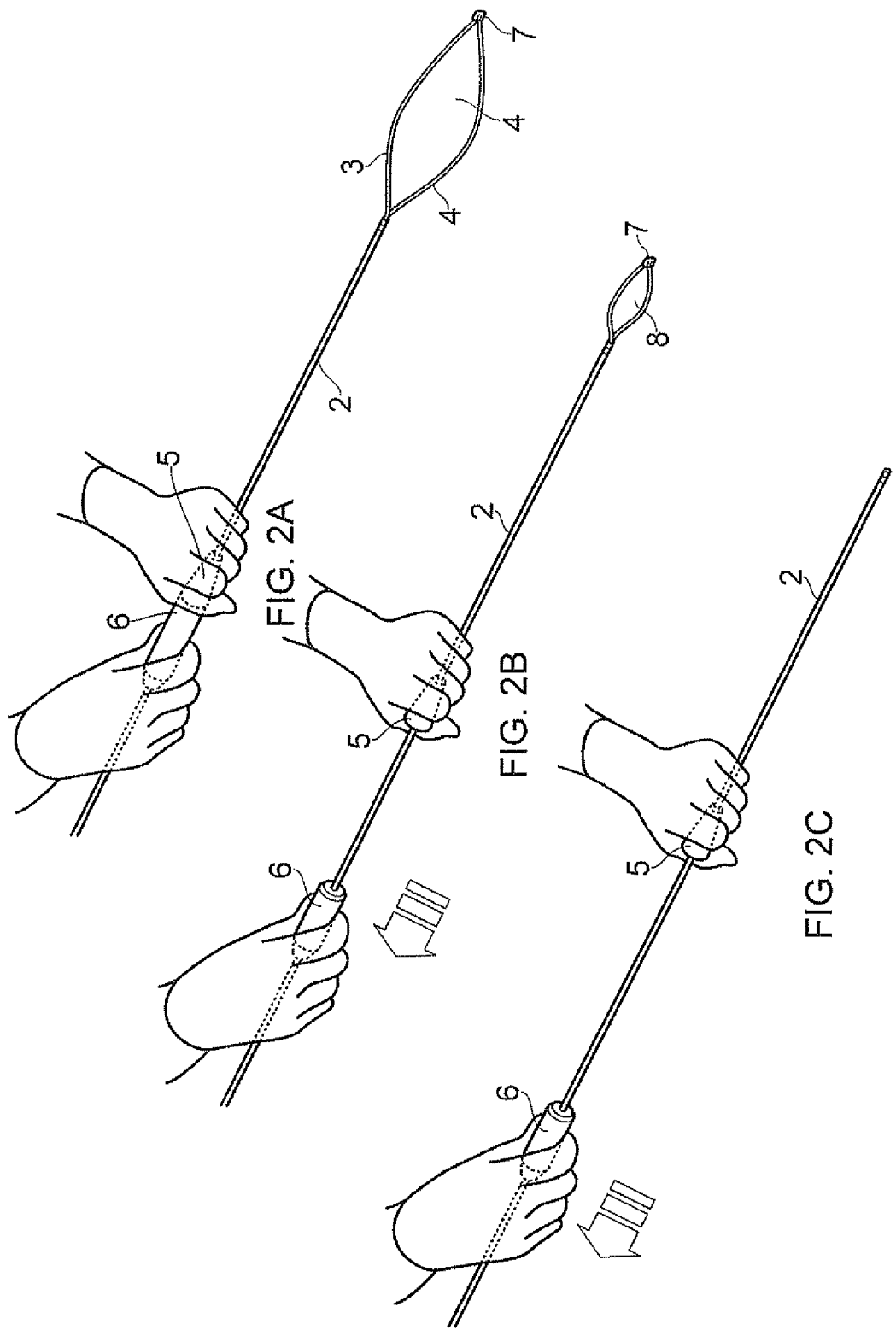
FIGS. 2A to 2C are schematic views of the bipolar snare of FIG. 1, shown in various stages of deployment.

Referring to FIGS. 1 & 2, a bipolar snare is shown generally at 1, and comprises an elongated tubular sheath 2 containing first and second wires 3 and 4. A first handle 5 is provided for maneuvering the sheath 2, and a second handle 6 is attached to the wires 3 & 4, such that longitudinal movement of the second handle 6 with respect to the first handle 5 causes the wires 3 & 4 to be moved longitudinally with respect to the sheath 2, as shown in FIGS. 2A, 2B & 2C.

An insulating connector 7 of a ceramic material joins the distal end of the first and second wires 3 & 4 one to the other, so as to form a loop shown generally at 8. The wires 3 & 4 are covered with an insulating covering 9 along the majority of their length, but are left exposed as shown at 10 and 11 towards their distal end.

Figure 3:
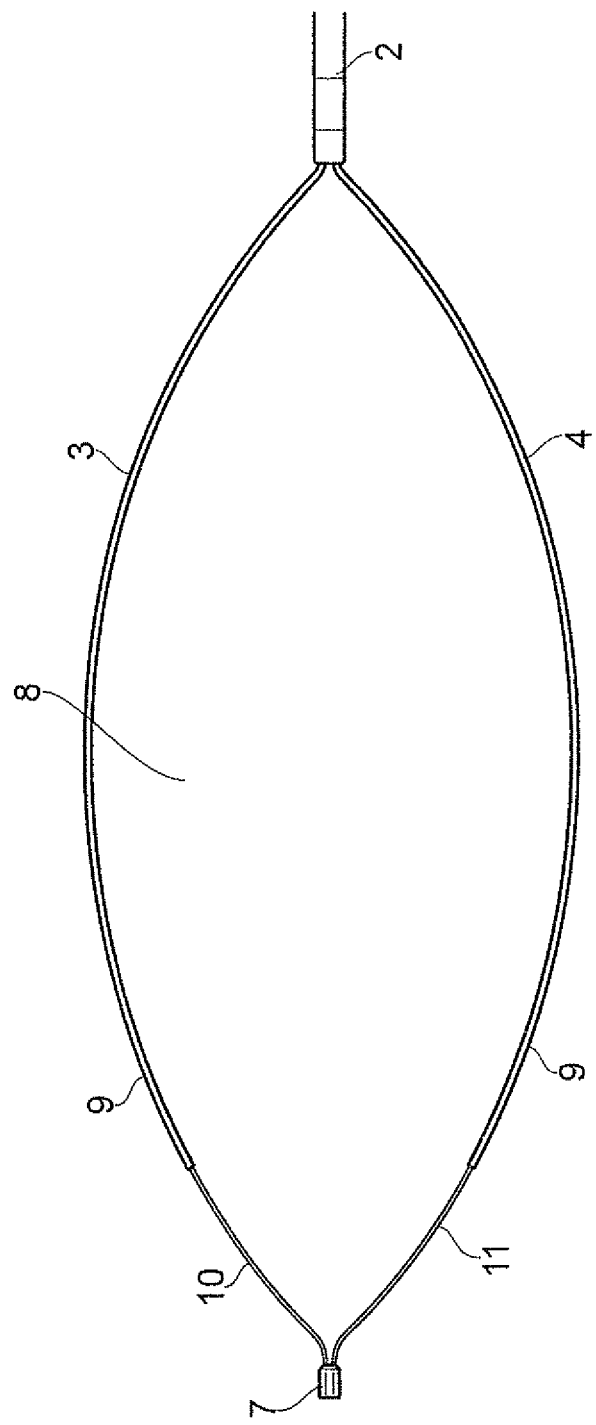
FIG. 3 is a side view of the distal end of the bipolar snare of FIG. 1, shown fully extended.
Figure 4:
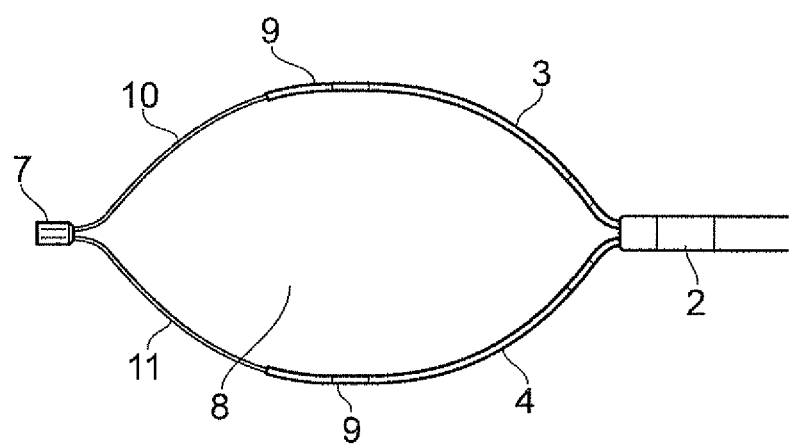
FIG. 4 is a side view of the distal end of the bipolar snare of FIG. 1, shown partially retracted.

When fully extended, the wires form a hexagonal shape as shown in FIGS. 1 & 3. This allows the loop 8 to be placed over a piece of tissue to be resected, such as a polyp or other small tissue mass, or alternatively over a much larger organ such as a female uterus (not shown). The handle 6 is then moved with respect to the handle 5, reducing the area of the loop 8 as shown in FIG. 4, and causing the exposed portions 10 and 11 to contact the tissue (not shown). The wires 3 & 4 are connected to the output of an electrosurgical generator (not shown) such that current flows between the exposed portions 10 & 11, thereby cutting the tissue. As the wires are withdrawn into the sheath 2, the exposed portions 10 & 11 continue to sever the tissue until the tissue is fully resected.

Figure 5:
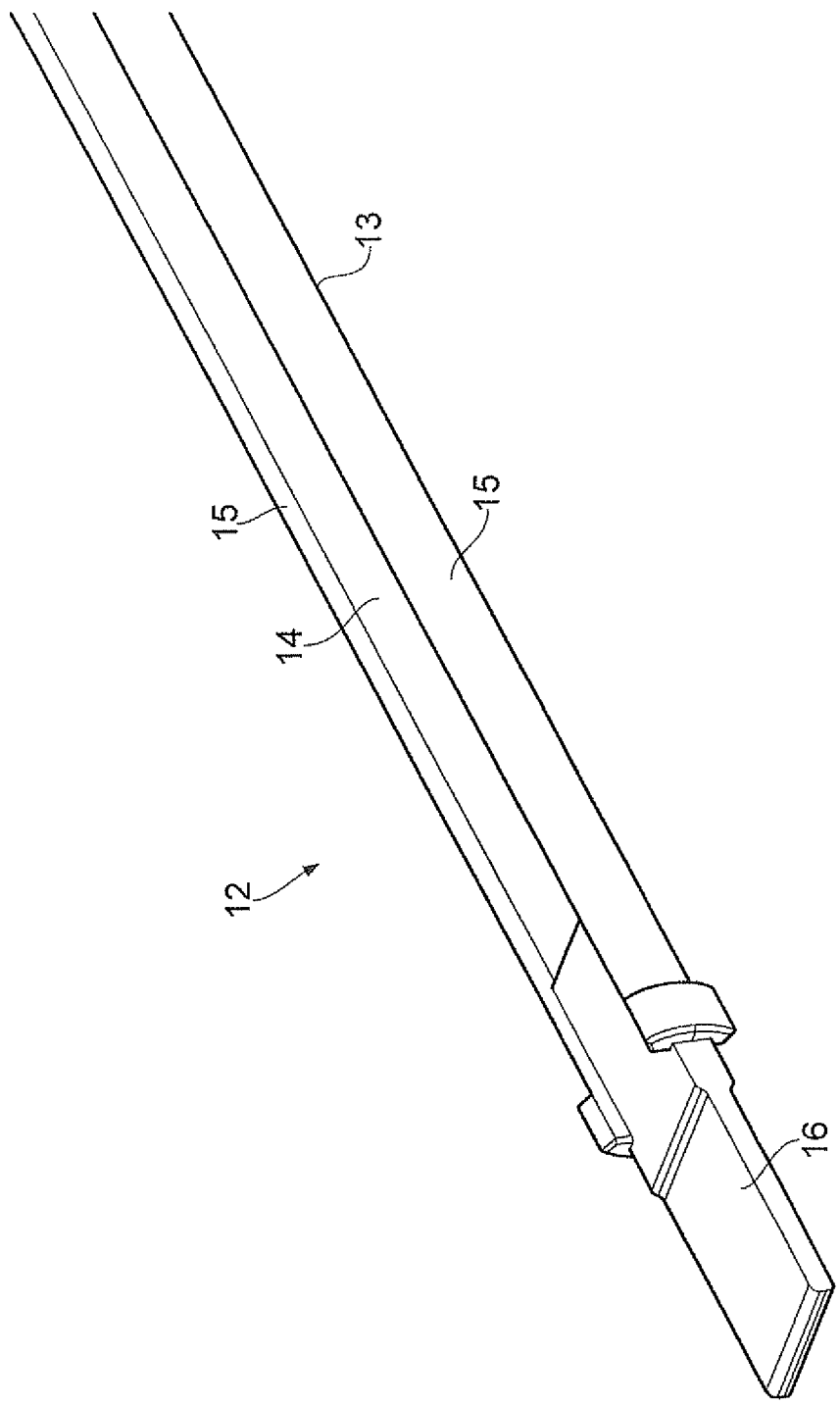
FIG. 5 is a perspective view of a guide member adapted to be present within the bipolar snare of FIG. 1.

FIG. 5 shows a guide member 12 which is located within the sheath 2. The guide member 12 includes an elongate member 13 having a generally I-shaped cross section, comprising a central divider 14 separated by two side sections 15. The side sections 15 are arcuate in shape such that the guide member can rotate within the sheath 2. The guide member 12 further includes a planar extension 16 provided at the distal end thereof. The central divider 14 is formed of a relatively hard plastics material such as nylon, while the extension 16 is formed of a softer plastics material such as silicone.

Figure 6:
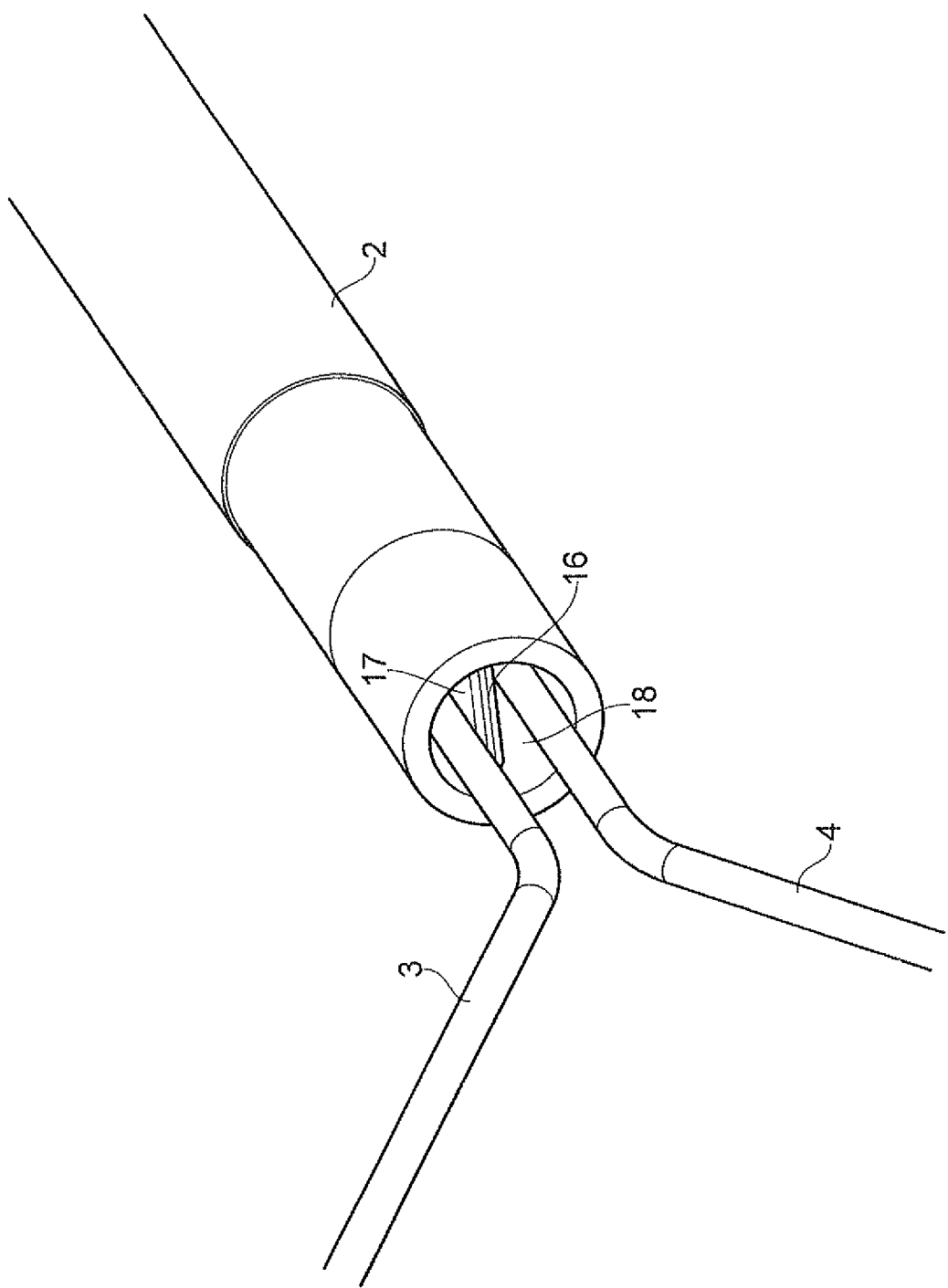
FIG. 6 is an enlarged perspective view of the distal end of the sheath of the bipolar snare of FIG. 1, showing the guide member within the sheath.
Figure 7:
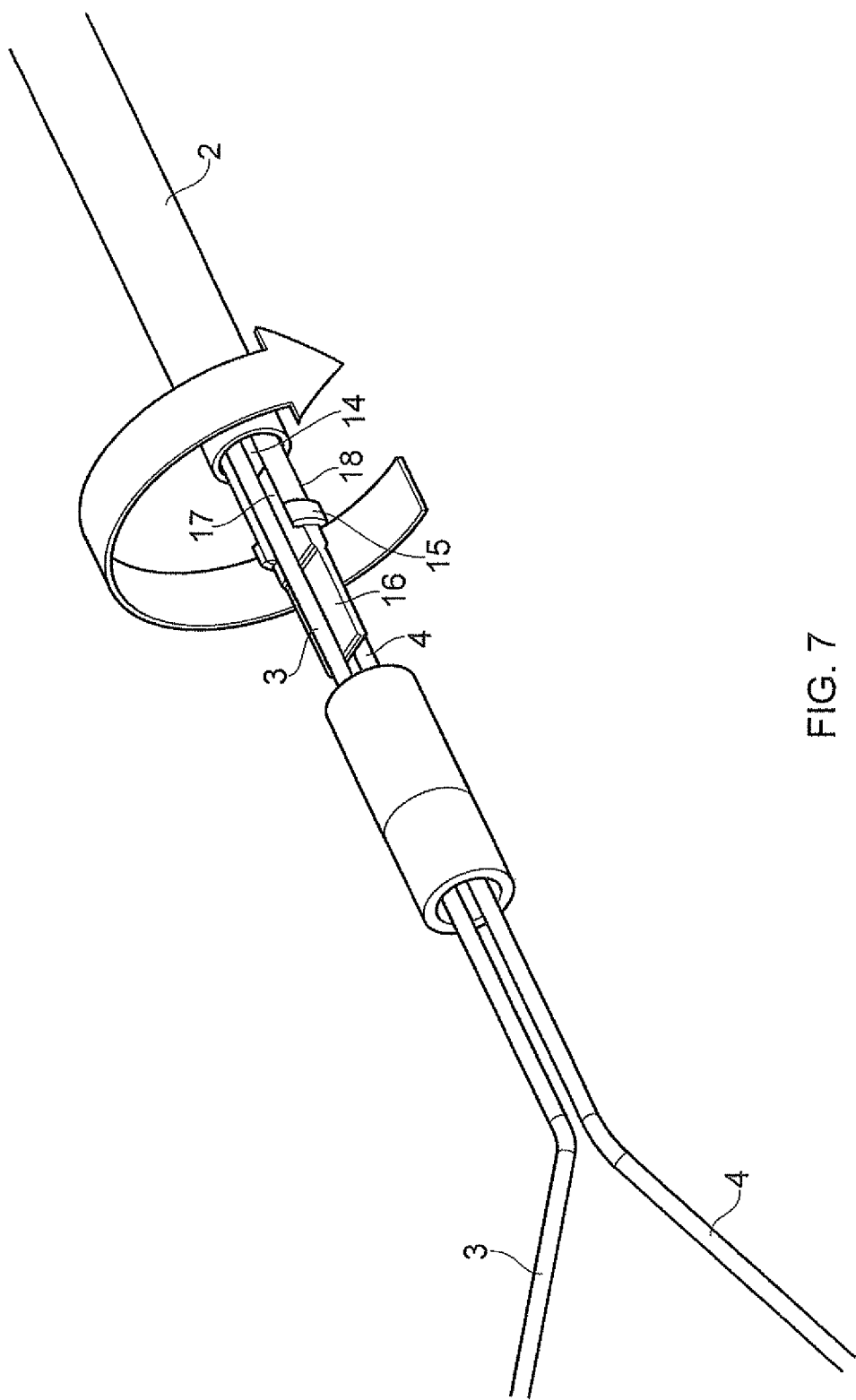
FIG. 7 is a perspective view of the distal end of the sheath of FIG. 1, showing the guide member being rotated within the sheath.

As shown in FIG. 6, the central divider 14 together with the extension 16 separates the space within the sheath into two compartments 17 & 18, such that the wire 3 is constrained within compartment 17, and the wire 4 is constrained within compartment 18. When the handle 6 is rotated with respect to the handle 5, the wires 3 & 4 are likewise rotated. Instead of the wires becoming twisted together, the guide member 12 rotates within the sheath 2 and the wires 3 & 4 remain separate from one another in their respective compartments 17 & 18. This is depicted in FIG. 7, with the distal end of the sheath 2 being shown displaced from its actual position in order to show the rotation of the guide member 12.

Figure 8:
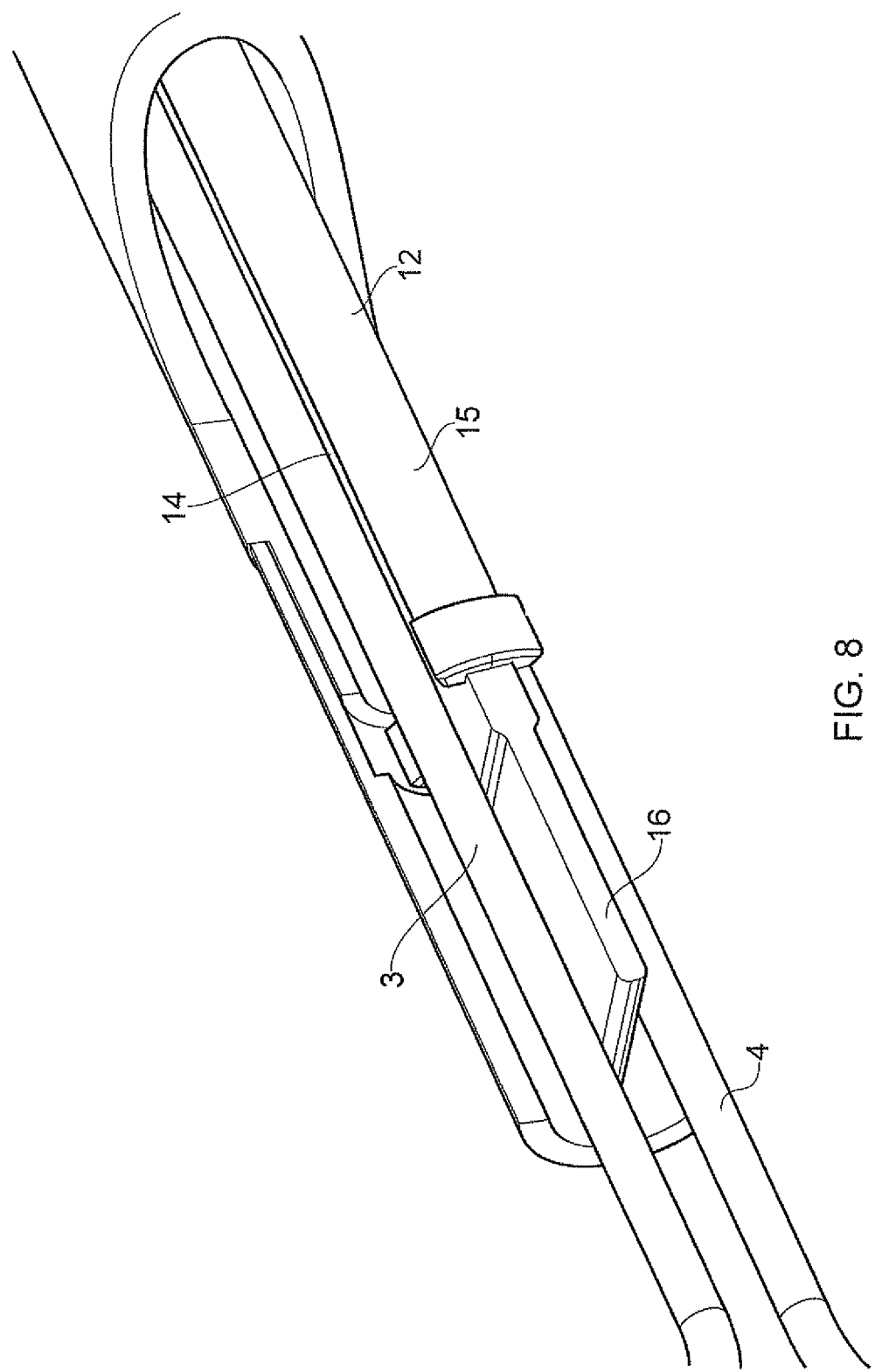
FIG. 8 is a perspective view of the distal end of the sheath of FIG. 1, shown partly in section, as the snare is being retracted.
Figure 9:
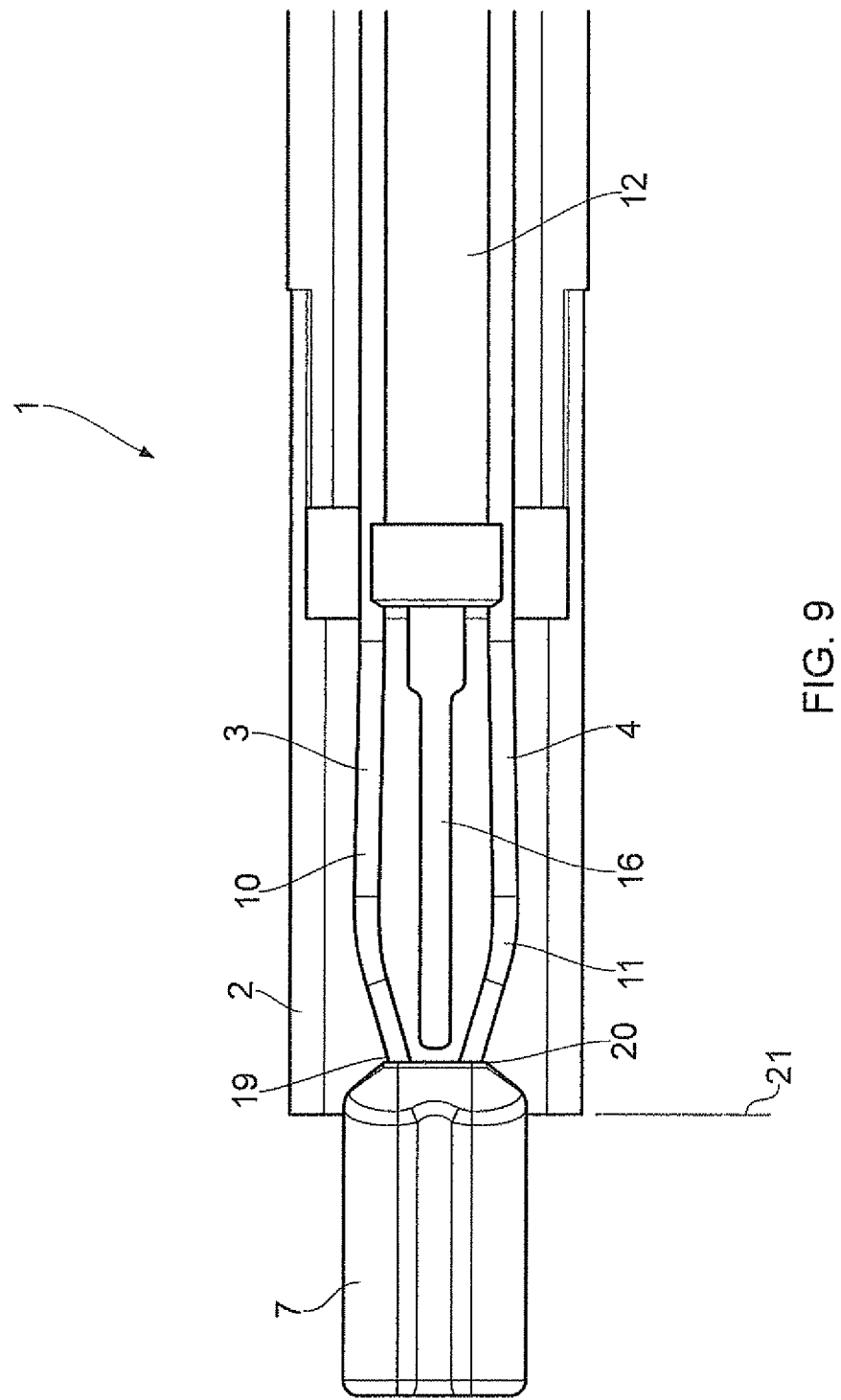
FIG. 9 is a sectional side view of the distal end of the sheath of FIG. 1, as the snare is being retracted.
Figure 10:
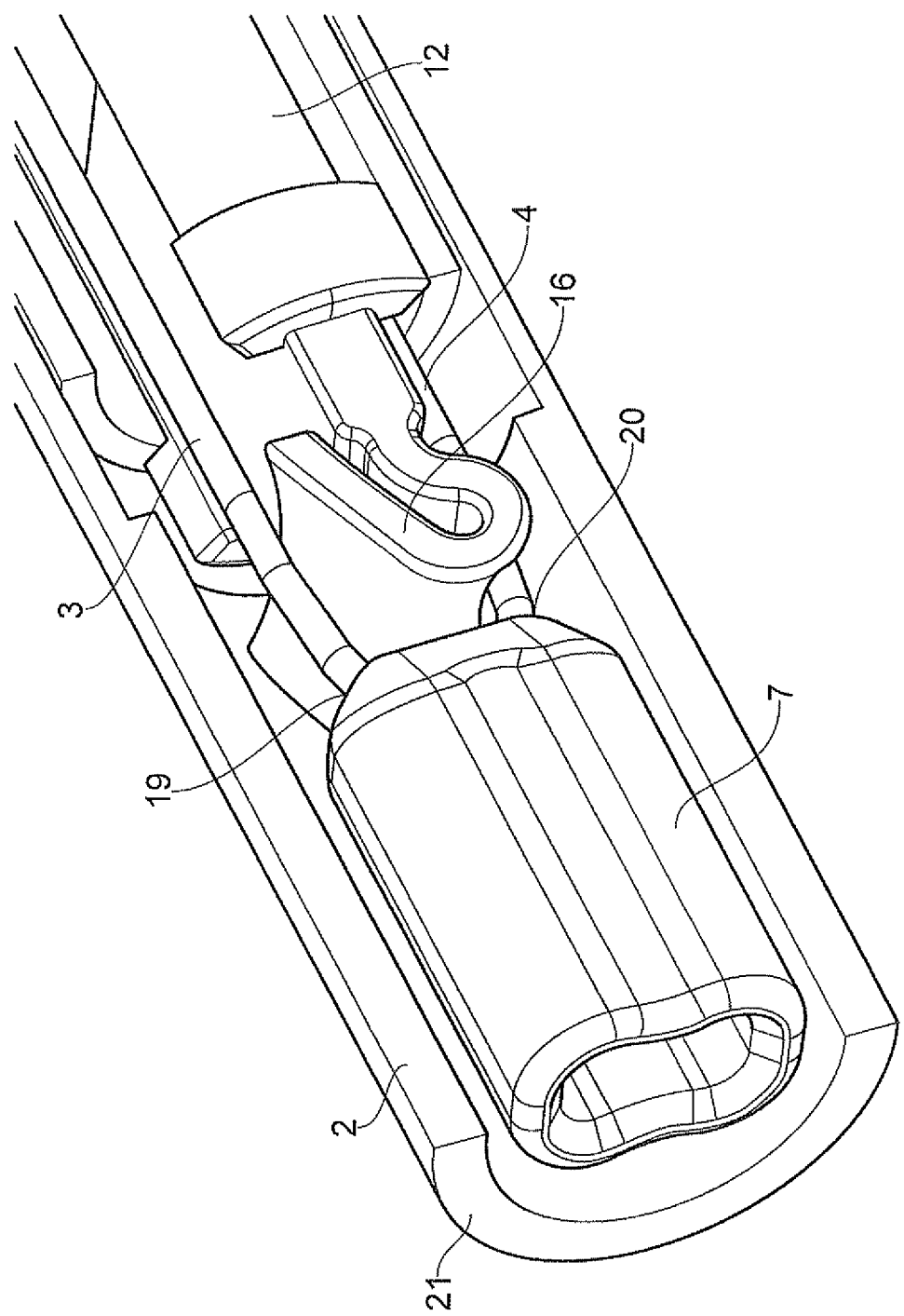
FIG. 10 is a perspective view of the distal end of the sheath of FIG. 1, partly in section, showing the snare fully retracted within the sheath.

FIG. 8 shows the wires 3 & 4 starting to be retracted within the sheath 2, with the central divider 14 together with the extension 16 keeping the wires apart. FIG. 9 shows the wires 3 & 4 being further retracted such that the insulating connector 7 is starting to enter the sheath 2. The wires 3 & 4 meet the insulating connector 7 at locations 19 & 20, which are at the same axial position with respect to each other. In FIG. 9, the locations 19 & 20 are already proximal of the end of the sheath 2, designated by axial position 21 in FIG. 9. As the wires are retracted further within the sheath, the ceramic connector 7 contacts the silicone extension 16 and causes it to flex, until it is collapsed into the position shown in FIG. 10, in which the connector 7 is fully contained within the sheath. As can readily be seen, extension 16 and the guide member 12 can still be rotated, even with the extension 12 in its collapsed position, maintaining the wires 3 & 4 separate even when they are fully received within the sheath 2.

Prior art bipolar snares often encounter difficulties in performing the cutting of the last section of tissue, especially when being used on large tissue masses or whole organs. This is because the loop cannot be reduced to zero, as the wires and the insulating connector joining them cannot be received within the sheath. This means that there is always some small section of the loop outside the sheath, and that consequently the cutting of tissue is incomplete. In such instances, the final act of resection is often carried out by the mechanical force of the wires on the tissue, as opposed to the more controlled electrosurgical action.

With the present invention, the wires 3 & 4, together with the locations 19 & 20 where they meet the insulating connector 7, are all retractable within the sheath, leaving no part of the loop 8 remaining outside. This ensures that the cutting of a tissue mass is completed by the electrosurgical action of the exposed portions 10 & 11 of the wires, as the wires 3 & 4 and the locations 19 & 20 where they meet the insulating connector 7 enter the sheath 2. Even though the exposed portions 10 & 11 of the wires are received within the sheath 2, contact therebetween and the consequent shorting of the wires is prevented by the guide member 12, even if the wires are rotated.

In other embodiments of the invention the guide member may be arranged in a different manner. For example, in one embodiment rather than have a flexible extension the guide member may simply be set back from the distal end of the sheath a sufficient amount to provide space for the loop and at least part of the connector to enter the sheath, to ensure that cutting can be completed. In another embodiment the guide member may be movable in some other way, for example, slidably backwards within the sheath, such that as the end of the loop and the connector approach and begin to enter the sheath the guide member is pushed backwards along and within the sheath by the loop and/or connector, again to provide space for the loop, at least, and preferably at least part of the connector to enter the sheath. Such a slidable guide member may be provided with a spring return to allow the guide to return to its normal, non-retracted, position when the loop is extended once again.

Various further modifications may be made to the above described embodiment, whether by way of addition, substitution, or deletion, to provide further embodiments any and all of which are intended to be encompassed within the scope of the appended claims.

The invention claimed is:

1. A bipolar snare device comprising
    an elongated tubular electrically insulating sheath having a proximal and a distal end,
    a pair of elongated flexible electrically conductive wires with the wires disposed within the sheath and each having proximal and distal ends and having a length such that the wires can each extend from at least the distal end of the sheath,
    an electrically insulating connector disposed at the distal ends of the wires mechanically connecting the distal ends of the wires to form a loop projecting from the distal end of the sheath and with the wires electrically insulated from each other,
    electrical insulation disposed covering all but a selected portion of each of the elongated wires which form the loop,
    a handle for sliding the wires relative to the sheath to expand or contract the loop, and
    electrical connections for connecting the proximal ends of the wires to a bipolar electrosurgical generator,
    wherein the device also includes a guide member located within the sheath and forming compartments for each of the electrically conductive wires, the guide member being rotatable within the sheath to prevent the electrically conductive wires from becoming twisted one about the other, the guide member being provided with an extension extending from the distal end of the guide member, the extension allowing the conductive wires to be longitudinally movable with respect to the extension to expand or contract the loop, and yet being capable of separating the electrically conductive wires as they exit the guide member.

2. A bipolar snare device according to claim 1, wherein the guide member comprises a cylindrical member with an I-shaped cross section forming two compartments, one for each of the electrically conductive wires.

3. A bipolar snare device according to claim 1, wherein the guide member comprises a cylindrical member with two lumens therein, one for each of the electrically conducting wires.

4. A bipolar snare device according to claim 1, wherein the extension is in the form of a planar partition.

5. A bipolar snare device according to claim 1, wherein the extension is movable between two positions, a first extended position in which it separates the electrically conductive wires, and a second retracted position to provide space for the electrically insulating connector to at least partly enter the sheath.

6. A bipolar snare device according to claim 3, wherein the extension is formed of a flexible material, capable of collapsing into its second position.

7. A bipolar snare device according to claim 1, wherein the guide member is set back from the distal end of the sheath.

8. A bipolar snare device according to claim 7, wherein the guide member is set back from the distal end of the sheath to an extent that a whole of the loop including at least part of the electrically insulating connector is capable of being received within the sheath.

9. A bipolar snare device according to claim 1, wherein first and second locations where the wires meet the electrically insulating connector are substantially at a same axial position with respect to one another.

\* \* \* \* \*